US007463759B2

(12) United States Patent
Klingensmith et al.

(10) Patent No.: US 7,463,759 B2
(45) Date of Patent: Dec. 9, 2008

(54) SYSTEM AND METHOD FOR VASCULAR BORDER DETECTION

(75) Inventors: Jon D. Klingensmith, Shaker Heights, OH (US); Anuja Nair, Cleveland Heights, OH (US); Barry D. Kuban, Avon Lake, OH (US); D. Geoffrey Vince, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 24 days.

(21) Appl. No.: 11/449,569

(22) Filed: Jun. 8, 2006

(65) Prior Publication Data

US 2007/0071326 A1 Mar. 29, 2007

Related U.S. Application Data

(63) Continuation of application No. 10/837,352, filed on Apr. 29, 2004, now Pat. No. 7,215,802.

(60) Provisional application No. 60/550,620, filed on Mar. 4, 2004.

(51) Int. Cl.
*G06K 9/00* (2006.01)
*A61B 5/02* (2006.01)

(52) U.S. Cl. .................. 382/128; 600/483; 600/485

(58) Field of Classification Search ......... 382/128–134, 382/199, 256; 128/916; 600/324, 407, 424, 600/431, 440, 443, 462, 467, 468, 469, 481–484, 600/500, 513, 542, 570; 604/532; 606/194
See application file for complete search history.

(56) References Cited

U.S. PATENT DOCUMENTS 4,478,219 A * 10/1984 Dujovny et al. ............. 606/158

5,657,760 A * 8/1997 Ying et al. ................... 600/439

(Continued)

FOREIGN PATENT DOCUMENTS

WO     WO 94/23652     10/1994

(Continued)

OTHER PUBLICATIONS

International Search Report dated Apr. 3, 2008, based on PCT/US2005/006159.

*Primary Examiner*—Abolfazl Tabatabai
(74) *Attorney, Agent, or Firm*—Leydig, Voit & Mayer Ltd.

(57) ABSTRACT

A system and method use the frequency spectrum of a radio frequency (RF) signal backscattered from vascular tissue to identify at least one border on a vascular image. A data gathering device is connected to a computing device and a transducer via a catheter. RF data generated via the transducer is provided to the computing device via the data-gathering device. The computing device includes: at least one data storage device for storing a plurality of tissue types and parameters related thereto, and at least one application (e.g., a characterization application, a gradient-border application, a frequency-border application and/or an active-contour application). The characterization application converts the RF data into the frequency domain and identifies a plurality of associate parameters. The identified parameters are compared to the parameters stored in the data storage device to identify the corresponding tissue type and thereafter determine at least one border on a vascular image.

27 Claims, 4 Drawing Sheets

U.S. PATENT DOCUMENTS

| | | | |
|---|---|---|---|
| 6,264,609 B1 * | 7/2001 | Herrington et al. | 600/443 |
| 6,381,350 B1 * | 4/2002 | Klingensmith et al. | 382/128 |
| 6,475,149 B1 * | 11/2002 | Sumanaweera | 600/441 |
| 6,615,071 B1 * | 9/2003 | Casscells et al. | 600/474 |
| 7,070,595 B2 * | 7/2006 | Ormsby et al. | 606/33 |
| 2004/0037455 A1 | 2/2004 | Klingensmith et al. | |
| 2005/0027188 A1 * | 2/2005 | Metaxas et al. | 600/410 |

FOREIGN PATENT DOCUMENTS

| | | |
|---|---|---|
| WO | WO 02/100249 | 12/2002 |
| WO | WO 2004/069027 | 8/2004 |

* cited by examiner

SYSTEM AND METHOD FOR VASCULAR BORDER DETECTION

CROSS-REFERENCE TO RELATED APPLICATIONS

This is a continuation of U.S. application Ser. No. 10/837,352, filed on Apr. 29, 2004, now U.S. Pat. No. 7,215,802 which claims the benefit pursuant to 35 U.S.C. § 119(e) of U.S. Provisional Patent Application No. 60/550,620, which was filed Mar. 4, 2004, both of which are incorporated herein, in their entirety, by reference.

BACKGROUND OF THE INVENTION

1. Field of the Invention

The present invention relates to vascular images, or more particularly, to a system and method of using the frequency spectrum of a radio frequency (RF) signal backscattered from vascular tissue to identify at least one border on a corresponding vascular image.

2. Description of Related Art

The present invention relates to medical imaging arts. It finds particular application to a system and method of identifying a border on a vascular image (e.g., intra-vascular ultrasound (IVUS) image, Virtual Histology™ (VH) image, etc.). It should be appreciated that while the present invention is described in terms of identifying a luminal and medial-adventitial border on an IVUS or VH image, the present invention is not so limited. Thus, for example, identifying any border (or boundary) on any vascular image is within the spirit and scope of the present invention.

Ultrasonic imaging of portions of a patient's body provides a useful tool in various areas of medical practice for determining the best type and course of treatment. Imaging of the coronary vessels of a patient by ultrasonic techniques can provide physicians with valuable information. For example, the image data may show the extent of a stenosis in a patient, reveal progression of disease, help determine whether procedures such as angioplasty or atherectomy are indicated or whether more invasive procedures may be warranted.

In a typical ultrasound imaging system, an ultrasonic transducer is attached to the end of a catheter that is carefully maneuvered through a patient's body to a point of interest such as within a blood vessel. The transducer may be a single-element crystal or probe that is mechanically scanned or rotated back and forth to cover a sector over a selected angular range. Acoustic signals are then transmitted and echoes (or backscatter) from these acoustic signals are received. The backscatter data can be used to identify the type of a scanned tissue. As the probe is swept through the sector, many acoustic lines are processed building up a sector-shaped image of the patient. After the data is collected, an image of the blood vessel (e.g., an IVUS image) can be reconstructed using well-known techniques. This image is then visually analyzed by a cardiologist to assess the vessel components and plaque content.

A typical analysis includes determining the size of the lumen and amount of plaque in the vessel. This is performed by generating an image of the vessel (e.g., an IVUS image) and manually drawing contoured boundaries on the image where the clinician believes the luminal and the medial-adventitial borders are located. In other words, the luminal border, which demarcates the blood-intima interface, and the medial-adventitial border, which demarcates the external elastic membrane or the boundary between the media and the adventitia, are manually drawn to identify the plaque-media complex that is located there between. This is a very time consuming process. Furthermore, this process is made more difficult when multiple images are being analyzed (e.g., to recreate a 3D vascular image, etc.) or the images are of poor quality (e.g., making the boundaries more difficult to see). Thus, it would be advantageous to have a system and method of identifying a border on a vascular image that overcomes at least one of these drawbacks.

SUMMARY OF THE INVENTION

The present invention provides a system and method of using the frequency spectrum of a radio frequency (RF) signal backscattered from vascular tissue to identify at least one border on a vascular image. Embodiments of the present invention operate in accordance with a data gathering device (e.g., an intra-vascular ultrasound (IVUS) device, etc.) electrically connected to a computing device and a transducer via a catheter. The transducer is inserted into a blood vessel of a patient and used to gather radio frequency (RF) data backscattered from vascular tissue. The RF data is then provided to (or acquired by) the computing device via the data-gathering device.

In a preferred embodiment of the present invention, the computing device includes at least one data storage device (e.g., database, memory, etc.) and at least one application (e.g., a characterization application, a gradient-border application, a frequency-border application and/or an active-contour application). A data storage device is used (at least primarily) to store a plurality of tissue types and related parameters. Preferably, the information is stored so that each tissue type is linked to at least one corresponding parameter.

In one embodiment of the present invention, the RF data (which is typically in the time domain) is provided to the characterization application, where it is converted (or transformed) into the frequency domain. The characterization application is then used to identify a plurality of parameters associated with the transformed RF data (or a portion thereof). The identified parameters are then compared to the parameters stored in the data storage device to identify the corresponding tissue type (or the type of tissue that backscattered the analyzed RF data). Such a process can be used, for example, to identify portions of RF data (or sets thereof) that are related to at least border-related tissue types (e.g., medial, adventitial, plaque, blood, etc.).

In another embodiment of the present invention, the characterization application is further used to identify parameters from the RF data (which is typically in the time domain). Parameters associated with the RF data (or a portion thereof) can be used, for example, to spatially identify certain frequencies (or parameters related thereto). Thus, for example, if a vascular wall comprises multiple tissue layers, corresponding RF data can be used to identify the location of these tissues and the related frequency spectrum can be used to identify tissue types.

The identified tissue types and corresponding RF data (or transformations thereof) (i.e., identified information) are provided to the active-contour application. The data is then used to identify at least one border on an image of a vascular object (e.g., intra-vascular ultrasound (IVUS) image, Virtual Histology™ (VH) image, etc.). For example, RF data corresponding to blood and plaque tissue can be used to identify (or substantially approximate) the luminal border on a vascular image. Similarly, RF data corresponding to plaque, medial and/or adventitial tissue can be used to identify (or substantially approximate) the medial-adventitial border on a vascular image.

In another embodiment of the present invention, the computing device further includes a frequency-border application. In this embodiment, the characterization application is adapted to provide the identified information to the frequency-border application, where it is used to determine spectral information. The spectral information is then provided to the active-contour application and used to determine at least one border on a vascular image (i.e., image-border data). In one embodiment of the present invention, the spectral information comprises spectral-force data, or data representing a frequency-based force that is applicable to (or a component of) the image-border data. In another embodiment of the present invention, the spectral-information comprises spectral-border data, or data representing an estimation of at least one border on a vascular image.

In one embodiment of the present invention, the computing device further includes a gradient-border application. The gradient-border application is adapted to use the acquired RF data to determine gradient information, which can then be used to identify a border or boundary. This is because a change in pixel color (e.g., light-to-dark, dark-to-light, shade1-to-shade2, etc) can indicate the presence of a border. In another embodiment of the present invention, the gradient information comprises gradient-force data, or data that represents a gradient-based force that is applicable to (or a component of) the image-border data. In another embodiment of the present invention, the gradient information comprises gradient-border data, or data that represents an estimation of at least one border on a vascular image (e.g., the IVUS image, a VH image, etc.). The gradient-border data can be used, for example, either alone or together with other border-related information (e.g., spectral information, etc.), to determine at least one border on a vascular image.

In another embodiment of the present invention, the active-contour application is further adapted to use other-border information to determine a border on a vascular image. In other words, information related to at least one border on another image(s) (e.g., a previous image, a subsequent image, multiple images, etc.) is used to determine (or approximate) at least one border on the vascular image at issue (i.e., the current vascular image). In another embodiment of the present invention, the active-contour application can be used to adjust the border to more closely match the actual border of the vascular object. This is done by considering, or taking into account continuity data, curvature data, and/or relatedness data.

In other embodiments of the present invention, the frequency-border application is further adapted to filter the transformed RF data before it is used to generate spectral information and the gradient-border application is further adapted to process the acquired RF data using traditional IVUS imaging techniques. A more complete understanding of the system and method of identifying a border on an IVUS image will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

The present invention provides a system and method of using the frequency spectrum of a radio frequency (RF) signal backscattered from vascular tissue to identify at least one border on a vascular image. In the detailed description that follows, like element numerals are used to describe like elements illustrated in one or more figures.

Figure 1:
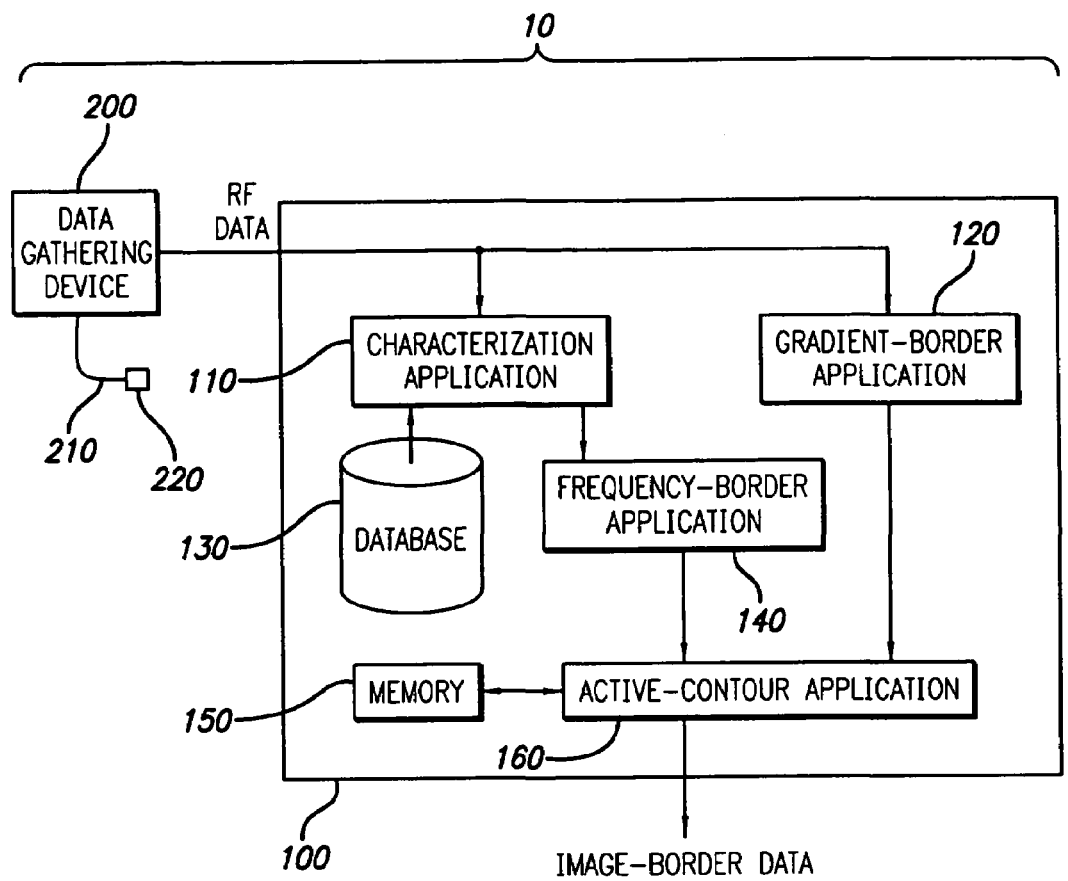
FIG. 1 illustrates a vascular-border-identification system in accordance with one embodiment of the present invention.

Embodiments of the present invention operate in accordance with a data-gathering device and a computing device electrically connected thereto. FIG. 1 illustrates a vascular-border-identification system 10 in accordance with one embodiment of the present invention. Specifically, a data-gathering console 200 is electrically connected to a computing device 100 and a transducer 220 via a catheter 210. The transducer 220 is inserted into a blood vessel of a patient (not shown) and used to gather radio frequency (RF) data backscattered from vascular tissue. The RF data is then provided to (or acquired by) the data-gathering device 200, where it is used (or can be used) to produce an image of the vessel (e.g., intra-vascular ultrasound (IVUS) image, etc.).

More particularly, RF data is typically gathered in segments, either through a rotating transducer or an array of circumferentially positioned transducers, where each segment represents an angular portion of the resultant image. Thus, it takes a plurality of segments (or a set of RF data) to image an entire cross-section of a vascular object. Furthermore, multiple sets of RF data are typically gathered from multiple locations within a vascular object (e.g., by moving the transducer linearly through the vessel). These multiple sets of data can then be used to create a plurality of two-dimensional (2D) images or one three-dimensional (3D) image. It should be appreciated that the data-gathering device 200 includes, but is not limited to, an IVUS console, thermographic device, optical device (e.g., an optical coherence tomography (OCT) console), MRI device, or any vascular imaging device generally known to those skilled in the art. It should further be appreciated that the computing device 100 depicted in FIG. 1 includes, but its not limited to, a personal computer or any other data-processing device (general purpose or application specific) that is generally known to those skilled in the art.

The RF data (or multiple sets thereof) is provided to (or acquired by) the computing device 100. In one embodiment of the present invention, the computing device 100 includes at least one data storage device (e.g., database 130, memory 150) and a plurality of applications (e.g., a characterization application 110, a gradient-border application 120, a frequency-border application 140 and/or an active-contour application 160). In a preferred embodiment of the present application, the RF data provided to (or acquire by) the computing device 100 is gated to electrocardiogram (ECG) information. The concept of gating RF data is in discussed in detail in U.S. patent application Ser. No. 10/647,977, which was filed Aug. 25, 2003, and is incorporated herein, in its entirety, by reference.

In a first embodiment of the present invention, a plurality of tissue types (e.g., medial, adventitial, plaque, blood, etc.) and related parameters are stored in a database 130. Preferably, the information is stored so that each tissue type is linked to its corresponding parameters. By doing so, each tissue type can be identified (or defined) by the parameters that are linked thereto. It should be appreciated that the term parameter, as that term is used herein, includes, but is not limited to maximum power, minimum power, frequencies at maximum and/or minimum power, y intercepts (estimated or actual), slope, mid-band fit, integrated backscatter, tissue depth, and all parameters (either time or frequency based) generally known to (or discernable by) those skilled in the art. It should further be appreciated that the methods used to acquire the parameters or their relationship to the tissue types (e.g., using scientific theory, experimentation, computer simulation, etc.) are not a limitation of the present invention. Is should also be appreciated that the term tissue type, as that term is used herein, includes, but is not limited to, blood tissue, plaque tissue (e.g., calcified tissues, fibrous tissues, calcified-necrotic tissues and fibro-lipidic tissues), medial tissue, adventitial tissue, and all other vascular tissues, or combinations thereof (e.g., medial-adventitial tissue), generally known to those skilled in the art. It should also be appreciated that the data storage devices depicted herein (e.g., database 130, memory 150) include, but are not limited to, RAM, cache memory, flash memory, magnetic disks, optical disks, removable disks, SCSI disks, IDE hard drives, tape drives and all other types of data storage devices (and combinations thereof, such as RAID devices) generally known to those skilled in the art.

As shown in FIG. 1, the RF data (which is typically in the time domain) is provided to the characterization application 110, where it is converted (or transformed) into the frequency domain. The characterization application 110 is then used to identify a plurality of parameters associated with the transformed RF data (or a portion thereof. The identified parameters are then compared to the parameters stored in the database 130 to identify the corresponding tissue type (or the type of tissue that backscattered the analyzed RF data). Such a process can be used (e.g., once or repeatedly) to identify the portions of RF data (or sets thereof) that are associated with each stored tissue type (e.g., medial, adventitial, plaque, blood, etc.).

It should be appreciated that the frequency conversion (or transformation) discussed herein includes, but is not limited to, the use of a fast Fourier transformation (FFT), the Welch periodogram, autoregressive power spectrum (AR) analysis, or any other frequency transformation or spectral analysis generally known to those skilled in the art. It should further be appreciated that the RF data may either be received in real-time (e.g., while the patient is in the operating room) or after a period of delay (e.g., via CD-ROM, etc.). It should also be appreciated that the identified parameters should be related (generally) to the stored parameters. Thus, for example, an estimated Y intercept parameter should be identified if data related to a signal's estimated Y intercept is stored in the database 130 and linked to at least one tissue type.

In a second embodiment of the present invention, the characterization application 110 is further used to identify parameters from the RF data (which is typically in the time domain). Parameters associated with the RF data (or a portion thereof can be used, for example, to spatially identify certain frequencies (or parameters related thereto). Thus, for example, if a vascular wall comprises multiple tissue layers, corresponding RF data can be used to identify the location of these tissues and the related frequency spectrum can be used to identify tissue types. The use of parameters to identify tissue types is discussed in detail in U.S. Pat. No. 6,200,268, which was issued on Mar. 13, 2001, and U.S. patent application Ser. No. 10/647,971, which was filed on Aug. 25, 2003, and are incorporated herein, in their entireties, by reference.

In either embodiment of the present invention, the RF data (or a transformation thereof) and the identified tissue types (including the association therebetween) are provided to the active-contour application 160. This data is then used to identify at least one border on an image of a vascular object (e.g., intra-vascular ultrasound (IVUS) image, Virtual Histology™ (VH) image, etc.). For example, RF data corresponding to blood and plaque tissue can be used to identify (or substantially approximate) the luminal border on a vascular image. Similarly, RF data corresponding to plaque, medial, and/or adventitial tissue can be used to identify (or substantially approximate) the medial-adventitial border on a vascular image.

It should be appreciated that the present invention is not limited to the identification of any particular border (or boundary) on a vascular image, and includes all borders generally known to those skilled in the art. It should further be appreciated that the applications depicted and discussed herein (e.g., characterization application 110, gradient-border application 120, frequency-border application 140, active-contour application 160), may exist as a single application or as multiple applications, locally and/or remotely stored. It should also be appreciated that the number and location of the components depicted in FIG. 1 are not intended to limit the present invention, and are merely provided to illustrate the environment in which the present invention may operate. Thus, for example, a computing device having a single data storage device and/or a remotely located characterization application (either in part or in whole) is within the spirit and scope of the present invention.

In another embodiment of the present invention, the computing device 100 further includes a frequency-border application 140. In this embodiment, the characterization application 110 is adapted to provide the RF data (or a transformation thereof) and the identified tissue types (including the association therebetween) to the frequency-border application 140, where it is used to determine spectral information. The spectral information is then provided to the active-contour application 160 and used to determine at least one border on a vascular image (i.e., image-border data).

In one embodiment of the present invention, the spectral information comprises spectral-force data. Spectral-force data is based (either directly or indirectly) on the information provided by the characterization application 110 and represents a frequency-based force that is applicable to (or a component of) the image-border data. The spectral-force data can be used, for example, to determine or refine the image-border data (e.g., as determined by the active-contour application 160). In other words, spectral-force data can be used together with other border-related information to determine a border on a vascular image, or applied to a border determined using border-related information (e.g., as an external force). Thus, the resultant border is based, at least in part, on the spectral-force data.

In one embodiment of the present invention, spectral-force data can be analogized to a gravitation field, in which the force (or field) is used to attract a border in a given direction, or to have a given shape. In this embodiment, the strength of the force (or gravitational pull) is directly proportional to the relatedness of the corresponding RF data to a border-related tissue type(s).

In another embodiment of the present invention, the spectral information comprises spectral-border data. Spectral-border data is based (either directly or indirectly) on the information provided by the characterization application 110 and represents an estimation of at least one border on a vascular image. The spectral-border data can be used, for example, either alone or together with other border-related information, to determine image-border data (e.g., as determined by the active-contour application 160). It should be appreciated that the term spectral information, as that term is used herein, is not limited to spectral-force data and/or spectral-border data, but further includes any data resulting from a spectral analysis of the acquired RF data.

In another embodiment of the present invention, the frequency-border application 140 is further adapted to filter the transformed RF data before it is used to generate spectral information. Specifically, in one embodiment of the present invention, a portion of the vascular object is selected. The corresponding transformed RF data and the information stored in the database 130 are then used to identify the tissue types that are related thereto. The minority tissue type is then filtered out. This can be accomplished, for example, by reassigning the RF data associated with the minority tissue type, so that it is associated with the majority tissue types. For example, if a first portion (or ninety-five percent) of the corresponding RF data is associate with blood tissue and a second portion (or fiver percent) of the corresponding RF data is associated with plaque tissue, then the second portion would be reassigned so that it is associate with blood tissue (i.e., making a homogenous composition). It should be appreciated, however, that the present invention is not limited to such a filtering algorithm, and includes any other filtering algorithms generally known to those skilled in the art.

Referring back to FIG. 1, in one embodiment of the present invention, the computing device 100 further includes a gradient-border application 120. The gradient-border application 120 is adapted to use the acquired RF data to determine gradient information, which can then be used to identify a border or boundary (e.g., used by the gradient-border application 120 to estimate at least one border, provided to the active-contour application and used together with spectral information to determine image-border data, etc.). This is because a change in pixel color (e.g., light-to-dark, dark-to-light, shade1-to-shade2, etc) can indicate the presence of a border.

Figure 2:
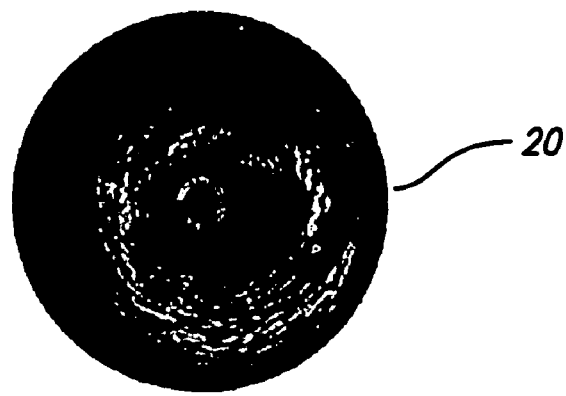
FIG. 2 illustrates an exemplary intra-vascular ultrasound (IVUS) image.

For example, FIG. 2 illustrates an exemplary IVUS image 20 of a vascular object. Starting from the center and working outward, the catheter can be identified by the first light-to-dark transition (or gradient). The catheter border is further identified in FIG. 3 (i.e., 330). Referring back to FIG. 2, and continuing outward, the next dark-to-light transition (or gradient) identifies the luminal border (see FIG. 3, 320). The medial-adventitial border can then be identified by going outward from the luminal border until the next dark-to-light transition (or gradient) is found (see FIG. 3, 310). It should be appreciated that because the IVUS image is constructed using gray-scales, it may be necessary to utilize an algorithm and/or at least one threshold value to identify precisely where the image changes from light to dark (or vice versa). However, it should further be appreciated that the present invention is not limited to any particular algorithm for identifying the aforementioned transitions, and includes all algorithms (and/or threshold values) generally known to those skilled in the art.

In another embodiment of the present invention, the gradient-border application 120 is further adapted to process the acquired RF data using traditional IVUS imaging techniques. For example, the gradient-border application 120 may be adapted to filter the RF data (e.g., using a highpass filter, etc.), detect relevant portions (e.g., envelope detection, etc.), and/or modulate any portion thereof (e.g., smoothing, log compressing, etc.). Such techniques are all well known to those skilled in the art. The resultant data can then be used to produce an IVUS image or determine gradient information.

In one embodiment of the present invention, the gradient information comprises gradient-force data. Gradient-force data is based (either directly or indirectly) on the gradients in an IVUS image and represents a gradient-based force that is applicable to (or a component of) the image-border data. The gradient-force data can be used, for example, to determine or refine the image-border data (e.g., as determined by the active-contour application 160). In other words, gradient-force data can be used together with other border-related information to determine a border on a vascular image, or applied to a border determined using border-related information (e.g., as an external force). Thus, the resultant border is based, at least in part, on the gradient-force data.

In one embodiment of the present invention, gradient-force data can be analogized to a gravitation field, in which the force (or field) is used to attract a border in a given direction, or to have a given shape. In this embodiment, the strength of the force (or gravitational pull), is directly proportional to the gradients in the IVUS image (or transitions therein).

In another embodiment of the present invention, the gradient information comprises gradient-border data. Gradient-border data is based (either directly or indirectly) on the gradients in an IVUS image and represents an estimation of at least one border on a vascular image (e.g., the IVUS image, a VH image, etc.). The gradient-border data can be used, for example, either alone or together with other border-related information (e.g., spectral information, etc.), to determine at least one border on a vascular image. It should be appreciated that the term gradient information, as that term is used herein, is not limited to gradient-force data and/or gradient-border data, but further includes any data resulting from an analysis of the gradients in an IVUS image.

In another embodiment of the present invention, the active-contour application 160 is further adapted to use other-border information to determine a border on a vascular image. In other words, information related to a border on another image (s) (e.g., a previous image, a subsequent image, multiple images, etc.) is used to determine (or approximate) at least one border on the vascular image at issue (i.e., the current vascular image).

Figure 3:
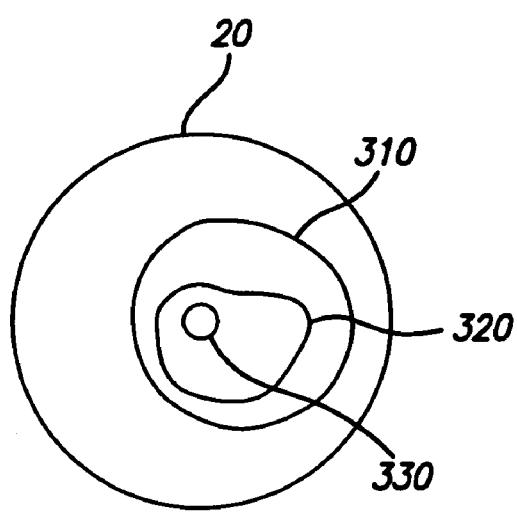
FIG. 3 illustrates a plurality of borders that are common to IVUS images.
Figure 4:
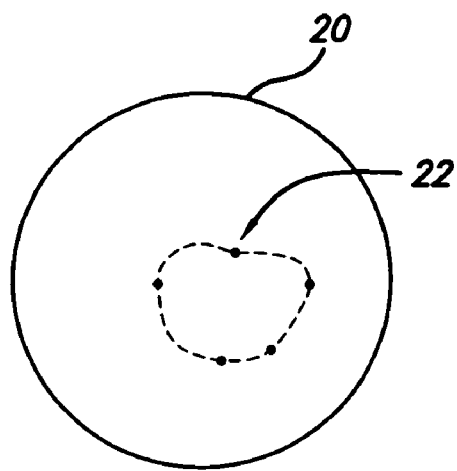
FIG. 4 illustrates a plurality of control points on one border of an IVUS image.

For example, in one embodiment of the present invention, the border-detection algorithm 160 is adapted to identify at least one control point on the border of another image. With reference to FIGS. 3 and 4, the border-detection algorithm can be used, for example, to identify a plurality of control points 22 on the luminal border 320. It should be appreciated that the location and number of control points depicted in FIG. 4 are not intended to limit the present invention, and are merely provided to illustrate the environment in which the present invention may operate. In an alternate embodiment, the active-contour application 160 is adapted to identify a border using user-identified control points. Such an embodiment is discussed in detail in U.S. Pat. No. 6,381,350, which was issued on Apr. 30, 2002, and is incorporated herein, in its entirety, by reference.

Figure 5:
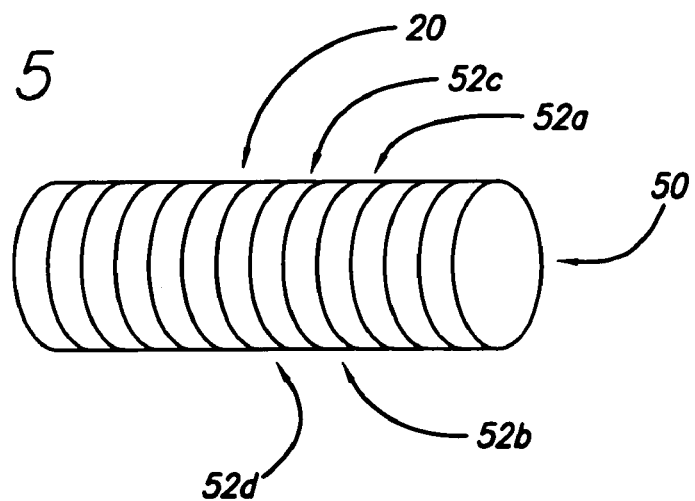
FIG. 5 illustrates how a plurality of 2D vascular images can be used to generate a 3D vascular image.

With reference to FIG. 1, once the border and control points are identified on another image, the active-contour application 160 can be used to identify at least one control point on the current vascular image. In one embodiment of the present invention, this is done by extrapolating the previously identified control points to the current vascular image. By doing this, multiple 2D images (or at least one 3D image) can be produced. For example, as illustrated in FIG. 5, multiple 2D images (e.g., 20, 52a-52d, etc.) are used to produce a 3D image of a tubular (e.g., vascular) object 50. It should be appreciated that a memory device 150 (see FIG. 1) can be used to store information related to this embodiment (e.g., a border on another image, control points on such a border, extrapolated control points, resulting image-border data, etc.).

Figure 6:
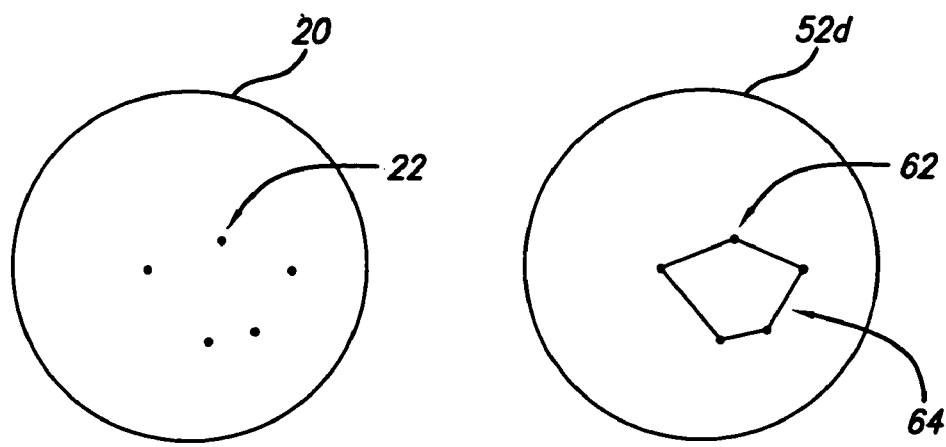
FIG. 6 illustrates how the control points from the image depicted in FIG. 4 can be extrapolated onto another image.

FIG. 6 illustrates one method as to how an identified control point can be extrapolated to the current vascular image. Specifically, the control points that were illustrated in FIG. 4 (i.e., 22) are extrapolated (or copied) to the current image (e.g., 52d), thus creating a second set of control points 62. In one embodiment of the present invention, the control points are extrapolated using Cartesian coordinates. It should be appreciated that, while FIG. 6 illustrates control points being extrapolated to an adjacent image, the present invention is not so limited. Thus, extracting control points to (or from) additional images (e.g., 52c, 52b, etc.) is within the spirit and scope of the present invention.

Once the control points are extrapolated, the active-contour application 160 is further adapted to identify (or approximate) a border based on the extrapolated points. For example, as shown in FIG. 6, the extrapolated points 62 may be connected using a plurality of lines 64, where the lines are either straight or curved (not shown). In another embodiment of the present invention, the extrapolating application is adapted to use an algorithm (e.g., a cubic-interpolation algorithm, etc.) to identify line shape. Border extrapolation is discussed in detail in U.S. patent application Ser. No. 10/647,473, which was filed Aug. 26, 2003, and is incorporated herein, in its entirety, by reference.

Referring back to FIG. 1, the active-contour application 160 is then used to adjust the border to more closely match the actual border of the vascular object. In doing so, the active-contour application 160 may consider, or take into account, at least (i) the proximity of the border to each extrapolated point (i.e., continuity or control-point factor), (ii) border curvature or smoothness (i.e., curvature or boundary factor), and/or (iii) the relationship between multiple borders (i.e., relatedness factor). For example, by considering a continuity or control-point factor, the border can be adjusted so that it passes through each extrapolated point. By considering a curvature or boundary factor, the border can be adjusted to prevent sharp transitions (e.g., corners, etc.). Furthermore, by considering a relatedness factor, multiple borders can be adjusted in relation to one another (e.g., the luminal border can always be located inside the medial-adventitial border, etc.).

In one embodiment of the present invention, these three factors are also used to determine related borders on adjacent images. It should be appreciated that if multiple factors are being considered, then individual factors may be weighted more heavily than others. This becomes important if the factors produce different results. It should further be appreciated that the present invention is not limited to the use of the aforementioned factors for border optimization, and that the use of additional factors to adjust (or optimize) a border is within the spirit and scope of the present invention.

In one embodiment of the present invention, the adjusted borders are configured to be manually manipulated. In other words, at least one point on the border can be selected and manually moved to a new location. The active-contour application 160 is then used (as previously discussed) to reconstruct the border accordingly. In another embodiment of the present invention, the active-contour application is further adapted to adjust related borders in adjacent images. This is done by fitting a geometrical model (e.g., a tensor product B-spline, etc.) over the surface of a plurality of related borders (e.g., as identified on multiple IVUS images). A plurality of points on the geometrical model are then parameterized and formulated into a constrained least-squares system of equations. If a point on the border is manually moved, the active-contour application can utilize these equations to calculate a resulting surface (or mesh of control points). The affected borders (e.g., adjacent borders) can then be adjusted accordingly.

Figure 7:
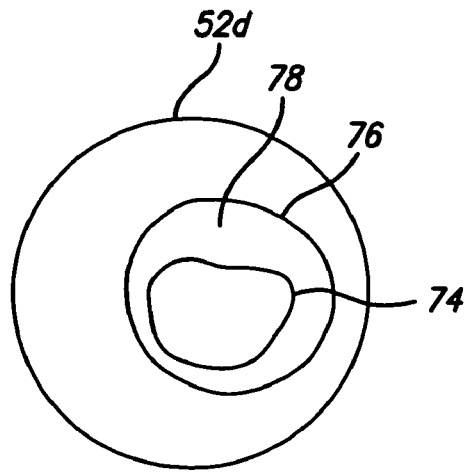
FIG. 7 illustrates a vascular image including a luminal boundary, a medial-adventitial boundary, and a plaque component located therebetween.

Once the border has been sufficiently adjusted, the aforementioned process can be repeated to identify additional borders. In an alternate embodiment of the present invention, multiple borders (e.g., luminal and medial-adventitial borders) are identified concurrently. In other words, the active-contour application 160, for example, can either be used (e.g., initiated) to identify a single border on a vascular image, thus requiring a subsequent use to identify another border on the vascular image, or used (e.g., initiated) to identify multiple borders on a vascular image. In the latter, the multiple borders are identified at substantially the same time. The multiple borders can then be imaged (in either 2D or 3D) and analyzed by either a skilled practitioner or a computer algorithm. For example, as illustrated in FIG. 7, the luminal border 74 and the medial-adventitial border 76 can be used (by either a clinician or an algorithm) to identify the plaque-media complex 78 of a vascular object.

Figure 8:
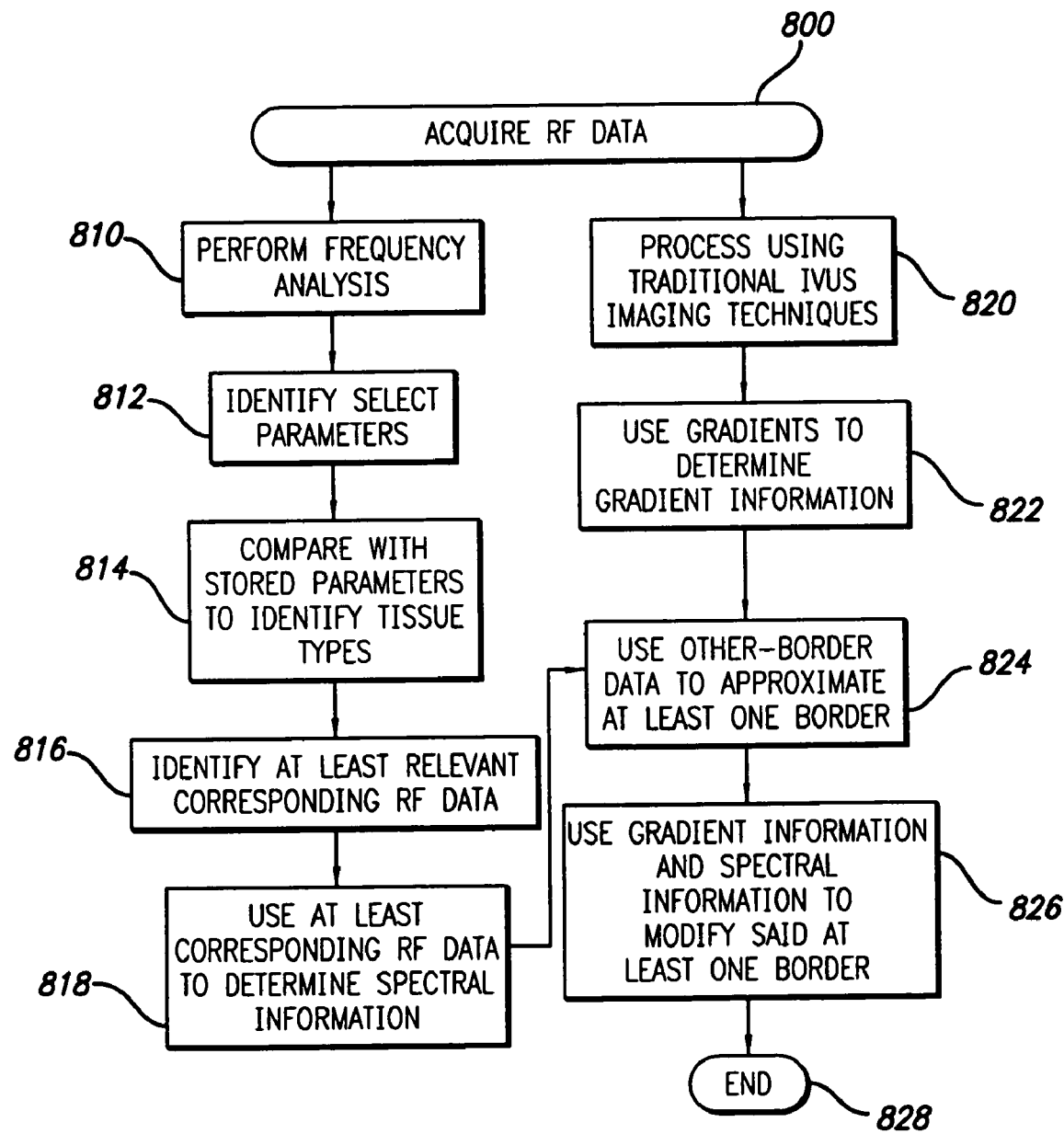
FIG. 8 illustrates a method of identifying a border of a vascular object in accordance with one embodiment of the present invention.

One method of identifying a border on a vascular image is illustrated in FIG. 8. Specifically, at step 800, RF data backscattered from vascular tissue is acquired. The RF data is then (i) transformed from the time domain into the frequency domain and (ii) processed using traditional IVUS imaging techniques, at steps 810 and 820, respectively. With respect to the transformed RF data, a plurality of parameters are identified at step 812, and compared to stored parameters, at step 814, to identify a plurality of tissue types. At step 816, RF data (or a transformation thereof) that corresponds to at least relevant (e.g., border-related) tissue types is identified. The corresponding RF data is then used to determine spectral information (e.g., spectral-force data, spectral-border data, etc.) at step 818.

With respect to the IVUS data, gradients are used to determine gradient information (e.g., gradient-force data, gradient-border data, etc.) at step 822. At step 824, other-border data (e.g., data related to at least one border on at least one other image) is used to approximate at least one border on the current vascular image. At step 826, the gradient information and spectral information are used to modify the at least one border on the current vascular image, ending the method at step 828. It should be appreciated that the present invention is not limited to the method illustrated in FIG. 8, and further includes all methods of operation generally described or suggested herein or discernable by one skilled in art. For example, a method that uses only spectral information to determine at least one border on a vascular image is within the spirit and scope of the present invention.

Having thus described preferred embodiments of a system and method of identifying a border on a vascular image, it should be apparent to those skilled in the art that certain advantages of the system have been achieved. It should also be appreciated that various modifications, adaptations, and alternative embodiments thereof may be made within the scope and spirit of the present invention. The invention is further defined by the following claims.

What is claimed is:

1. A method of identifying borders on an image of a vascular object, comprising:
acquiring RF signal segment data backscattered from vascular tissue wherein individual ones of the RF signal segments represent an angular portion of the image;
transforming said RF signal segment data from time domain data to RF signal segment frequency domain data;
identifying a plurality of parameters of the RF signal segment frequency domain data;
using said plurality of parameters and previously stored data to identity at least a first portion and a second portion of said RF signal segment data that corresponds to a blood portion and a non-blood portion of said vascular tissue, respectively; and
determining a blood to non-blood border on said image of said vascular object in accordance with said first portion and said second portion of said RF signal segment data.

2. The method of claim 1, wherein the non-blood portion of said vascular tissue corresponds to a plaque portion of said vascular tissue.

3. The method of claim 1, wherein said step of determining said blood to non-blood border further comprises determining the luminal border on said image of said vascular object in accordance with said first and second portions of said RF signal segment data.

4. The method of claim 3 further comprising using said plurality of parameters and previously stored data to identify at least a third portion of said RF signal segment data that corresponds to at least a third tissue type of said vascular tissue, said third tissue type being selected from a list of tissue types consisting of medial tissue and adventitial tissue; and determining the medial-adventitial border on said image of said vascular object in accordance with said second and third portion of said transformed RF data.

5. The method of claim 4, wherein said third tissue type corresponds to both medial and adventitial tissues.

6. The method of claim 1, wherein said step of determining said border further comprises determining said border on said image of said vascular object in accordance with gradient information, said gradient information being derived from said RF signal segment data.

7. The method of claim 6, wherein said gradient information further comprises gradient-force data and gradient-border data.

8. The method of claim 1, further comprising the step of using other-border data from at least one other image of said vascular object to approximate said blood to non-blood border on said image of said vascular object.

9. The method of claim 8, wherein said step of determining said border further comprises determining said border on said image of said vascular object in accordance with gradient information, said gradient information being derived from said RF signal segment data.

10. The method of claim 1, further comprising the step of filtering said first and second portions of said RF signal frequency domain data before they are used to determine said blood to non-blood border.

11. The method of claim 10, wherein said step of filtering further comprises filtering said second portion of said RF signal segment frequency domain data to reduce the amount of non-blood particles visible in an image or sate second portion of said RF signal segment data.

12. The method of claim 11, wherein said step of filtering further comprises filtering said first portion of said RF signal segment frequency domain data to reduce the number of tissue types visible in an image of said first portion of said RF signal segment data.

13. The method of claim 1, wherein said step of determining said blood to non-blood border further comprises determining said blood to non-blood border on said image of said vascular object in accordance with spectral-force data and spectral-border data, said spectral-force data and said spectral-border data being derived from said RF signal segment frequency domain data.

14. The method of claim 1, wherein said step of determining said blood to non-blood border further comprises determining said blood to non-blood border on said image of said vascular object in accordance with at least one algorithm, said at least one algorithm being selected from a list of algorithms consisting of a continuity algorithm, a curvature algorithm, and a relatedness algorithm.

15. The method of claim 1, wherein said step of transforming said RF signal segment data further comprises transforming said RF signal segment data into the autoregressive (AR) frequency power spectrum.

16. The method of claim 1, wherein said step of identifying a plurality of parameters further comprises identifying at least one parameter of said RF signal segment frequency domain data, from a list of parameters consisting of maximum power, minimum power, frequency at maximum power, frequency at minimum power, y intercept, slope, mid-band fit, and integrated backscatter.

17. The method of claim 1, wherein said step of acquiring RF signal segment data further comprises acquiring RF signal segment data that is both backscattered from said vascular tissue and gated to electrocardiogram (ECG) information.

18. The method of claim 1 further comprising identifying at least one parameter of said RF signal segment data.

19. The method of claim 18, wherein said at least one parameter of said RF signal segment data comprises tissue depth.

20. A method of identifying at least one boundary on a vascular image, comprising:
acquiring RF signal segment data backscattered from vascular tissue wherein individual ones of the RF signal segments represent an angular portion of the image;
transforming said RF signal segment data from time domain data to frequency domain data;
identifying at least one parameter of said RF signal segment frequency domain data;
using said at least one parameter and previously stored data to identify at least one tissue type and RF signal segment frequency domain data corresponding thereto;
using said RF signal segment data to determine gradient information pertaining to said at least one boundary on said vascular image; and
using at least said gradient information and said corresponding RF signal segment data to determine said at least one boundary on said vascular image.

21. The method of claim 20, wherein said step of using at least said gradient information and said corresponding RF signal segment data further comprises using at least said gradient information and said RF signal segment frequency domain data to determine said at least one boundary on said vascular image.

22. The method of claim 20, wherein said at least one parameter is selected from a list of parameters consisting of maximum power, minimum power, frequency at maximum power, frequency at minimum power, y intercept, slope, midband fit, and integrated backscatter.

23. The method of claim 20, wherein said step of using said at least said gradient information and said corresponding RF signal segment data further comprises using other-boundary data to determine said at least one boundary on said vascular image.

24. The method of claim 23, further comprising the step of using said corresponding RF signal segment data to determine spectral-force data and spectral-boundary data, wherein at least said spectral-force data, said spectral-boundary data, and said gradient information are used to determine said at least one boundary on said vascular image.

25. The method of claim 24, further comprising the step of using said gradient information to determine gradient-force data and gradient-border data, wherein at least said gradient-force data, said spectral-force data, said gradient-border data, and said spectral-border data are used to determine said at least one boundary on said vascular image.

26. The method of claim 24, further comprising the step of filtering said corresponding RF signal segment data before it is used to determine said spectral-force data and said spectral-boundary data.

27. The method of claim 23, further comprising the step of using said gradient information to determine gradient-force data and gradient-border data, wherein at least said gradient-force data, said gradient-boundary data and corresponding RF signal segment data are used to determine said at least one boundary on said vascular image.

* * * * *